US012262889B1

(12) United States Patent
Zeiner et al.

(10) Patent No.: US 12,262,889 B1
(45) Date of Patent: Apr. 1, 2025

(54) SLIDING COMPRESSION RETAINERS FOR STAPLE CARTRIDGES WITH IMPLANTABLE ADJUNCTS

(71) Applicant: CILAG GMBH INTERNATIONAL, Zug (CH)

(72) Inventors: Mark Zeiner, Loveland, OH (US); Sarah Alexandra Scully, Cincinnati, OH (US); Miah Igwe, Cincinnati, OH (US); Brian Rountree, Maineville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/505,766

(22) Filed: Nov. 9, 2023

(51) Int. Cl.
*A61B 17/072* (2006.01)

(52) U.S. Cl.
CPC .. *A61B 17/072* (2013.01); *A61B 2017/07271* (2013.01)

(58) Field of Classification Search
CPC ........ A61B 17/07292; A61B 17/07207; A61B 17/068; A61B 2017/00951; A61B 2017/00004; A61B 2017/00893
See application file for complete search history.

(56) References Cited

U.S. PATENT DOCUMENTS

| 9,351,730 | B2 | 5/2016 | Schmid |
| 2016/0278764 | A1* | 9/2016 | Shelton, IV ......... A61B 17/105 |
| 2016/0278771 | A1* | 9/2016 | Shelton, IV ..... A61B 17/07292 |
| 2016/0278776 | A1* | 9/2016 | Shelton, IV ......... A61B 17/072 |
| 2016/0278777 | A1* | 9/2016 | Shelton, IV ......... A61B 17/105 |

\* cited by examiner

*Primary Examiner* — Nathaniel C Chukwurah
(74) *Attorney, Agent, or Firm* — TROUTMAN PEPPER LOCKE LLP

(57) ABSTRACT

Retainers and retainer systems for staple cartridges with implantable adjuncts are disclosed. The retainers and retainer systems enable a compressive force to be applied to implantable adjuncts on staple cartridges.

20 Claims, 13 Drawing Sheets

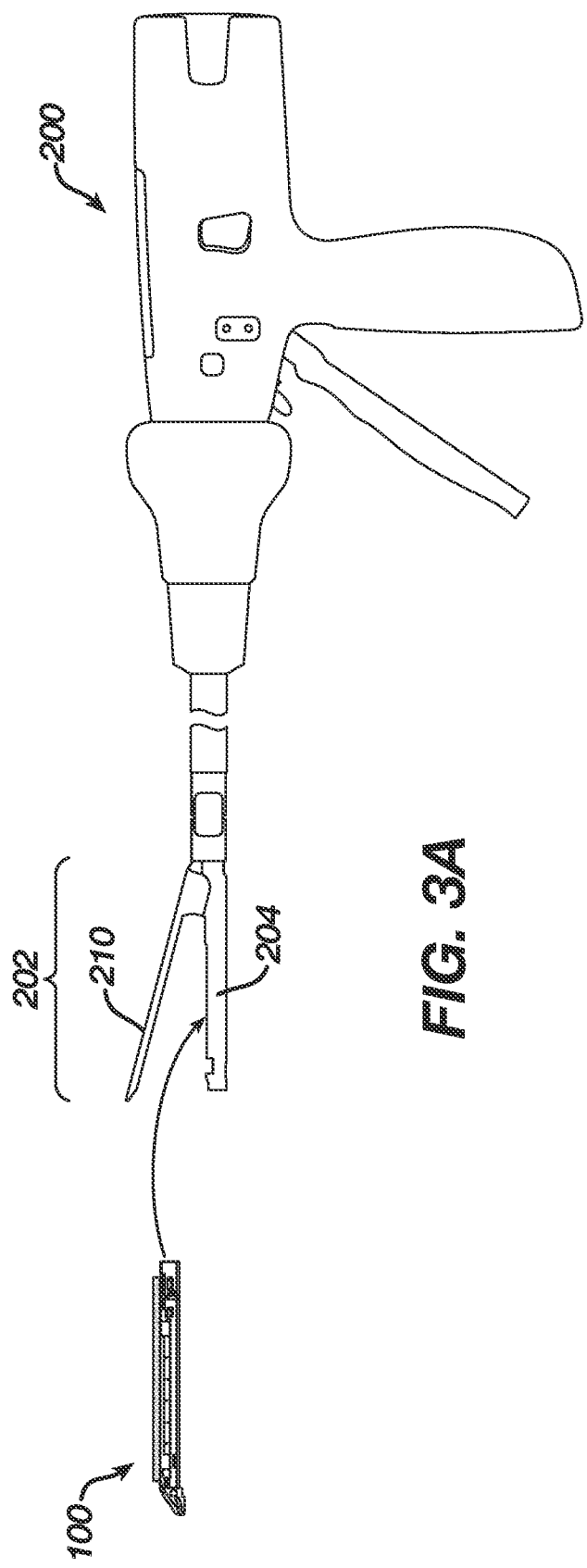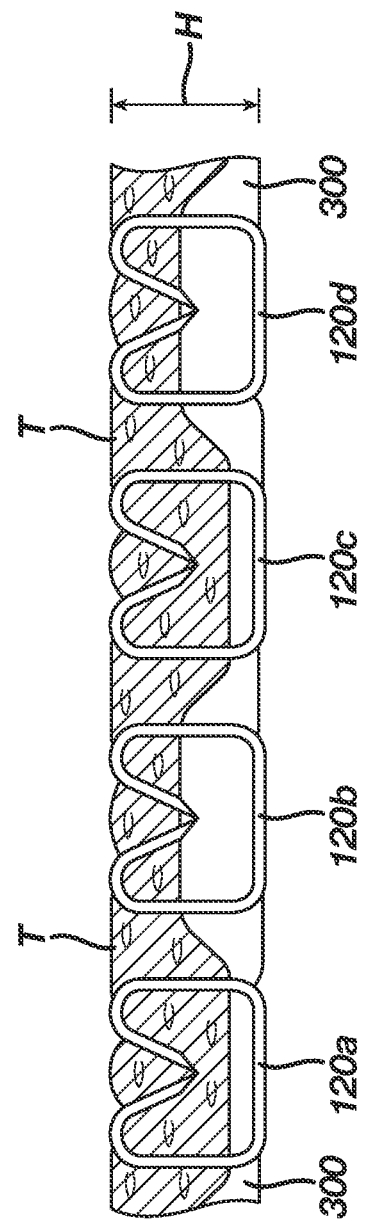
FIG. 3A
FIG. 3B

SLIDING COMPRESSION RETAINERS FOR STAPLE CARTRIDGES WITH IMPLANTABLE ADJUNCTS

FIELD OF INVENTION

The present disclosure generally relates to retainers and retainer systems for staple cartridges with implantable adjuncts. More specifically, the present disclosure relates to retainers and retainer systems that enable a compressive force to be applied to implantable adjuncts on staple cartridges.

BACKGROUND

Stapling is a crucial aspect of many surgical procedures, such as gastrointestinal, thoracic, and gynecological surgeries. Staple cartridges used in said stapling procedures may include an implantable adjunct on the deck of the cartridge. Care must be taken to ensure the implantable adjunct is properly adhered to the deck so that it is not dislodged from the deck during shipment or, importantly, during surgery before the adjunct is positioned at the treatment site.

SUMMARY

It is an object of the present designs to provide devices and methods to meet the above-stated needs. The designs can be for systems and devices for protecting an implantable adjunct on a staple cartridge, while also providing structure to allow compression of the adjunct to the deck of the staple cartridge before being used in surgery.

The disclosed technology includes a staple cartridge comprising an elongate body. The elongate body comprises a deck and the deck defines a plurality of staple pockets. Each of the staple pockets is accessible via an opening defined by the deck. The staple cartridge further comprises an implantable adjunct that is removably secured to the deck and a retainer removably securable to the elongate body.

The retainer is moveable through a range of motion relative to the elongate body while the retainer is secured to the elongate body. With the retainer secured to the elongate body, the implantable adjunct is positioned intermediate the retainer and the elongate body. A movement of the retainer through at least a portion of the range of motion can compress the implantable adjunct against the deck of the elongate body.

The staple cartridge further comprises a cam that is movably connected to the elongate body when the retainer is secured to the elongate body. The cam is positioned and arranged to selectively actuate the retainer along the range of motion. With the retainer secured to the elongate body, the cam is actuatable from a first position to a second position to actuate the retainer along the range of motion.

The disclosed technology includes a method of causing a retainer to compress an implantable adjunct against a deck of an elongated body. The method comprises actuating a cam between a first position and a second position to actuate a retainer of a staple cartridge along a range of motion relative to an elongate body of the staple cartridge, thereby causing the retainer to compress an implantable adjunct against a deck of the elongate body.

The method includes removing the cam from the retainer and removing the retainer from the elongate body. The method includes inserting the elongate body into a channel of an end effector.

The disclosed technology includes a staple cartridge comprising an elongate body. The elongate body has a deck and the deck defines a plurality of staple pockets. Each of the staple pockets is accessible via an opening defined by the deck. The staple cartridge includes an implantable adjunct that removably secured to the deck and a retainer that is removably securable to the elongate body. The retainer is configured to compress the implantable adjunct against the deck of the elongate body. The staple cartridge includes a cam that has a lumen extending therethrough. The lumen is configured to at least partially receive the elongate body, the implantable adjunct, and the first retainer and to cause the first retainer to compress the implantable adjunct against the deck of the elongate body.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

FIG. 3A is a side-view schematic of a staple cartridge being loaded into a surgical instrument, according to aspects of the present disclosure.

FIG. 3B is a schematic view of an implantable adjunct stapled to tissue, according to aspects of the present disclosure.

DETAILED DESCRIPTION

Figure 1:
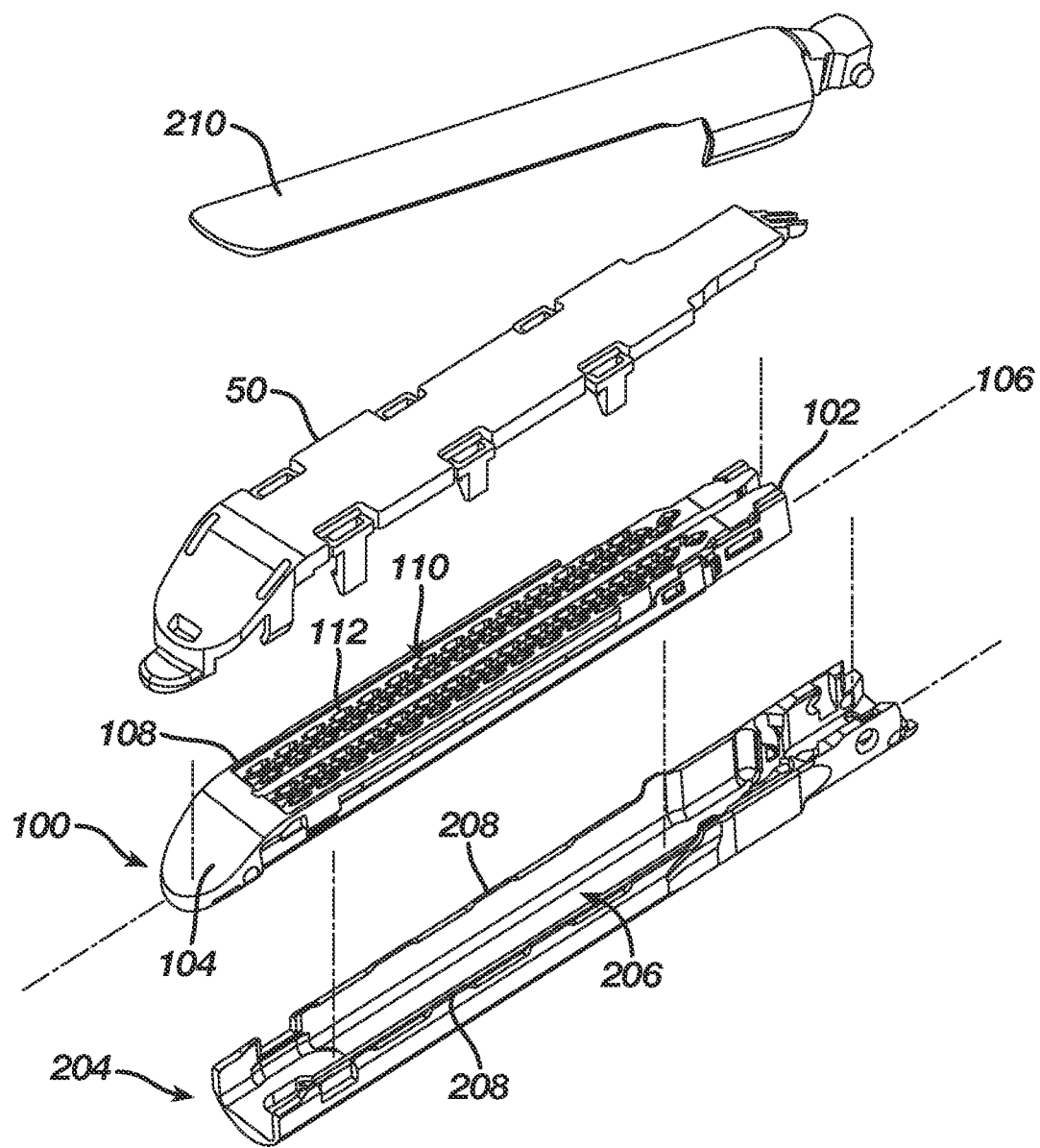
FIG. 1 is a perspective view of a replaceable staple cartridge without an adjunct.

Specific examples of the present invention are now described in detail with reference to the Figures, where identical reference numbers indicate elements which are functionally similar or identical. The examples provide solutions for staple cartridge systems that include an implantable adjunct. An implantable adjunct can be used in stapling surgery to account for differing tissue thicknesses across the length of the stapling surface. For instance, a length of tissue clamped in an end effector of a surgical instrument may by thicker at one end of the staple cartridge that at the other end. However, the staple cartridge may be loaded with staples of a single length, meaning the staples may be properly sized for the thicker section of tissue, but may be too long for the thinner section of tissue. If the staples are too long, proper compression of the tissue at the staple site may not be optimal. An implantable adjunct can account for this differing tissue thickness by providing support for the thinner sections of tissue. Where the tissue is thick, the implantable adjunct can be compressed all the way down since no additional thickness is needed to account for the staple length. Where the tissue is thin, the implantable adjunct is not as compressed, meaning the adjunct provides the additional thickness needed to account for the staple length, thereby providing proper compression in that section of the tissue.

The implantable adjunct must be properly, yet reversibly, adhered to the deck of the staple cartridge so that it does not become dislodged during shipment or, importantly, during the surgical procedure. For instance, during surgery the staple cartridge is loaded into an end effector of a cutter/stapler surgical instrument, sent through a cannula to a surgical site, traversed through and around tissue, and then positioned at the target tissue site that will be cut and stapled by the surgical instrument. If the implantable adjunct is not properly adhered to the deck of the staple cartridge, it may become dislodged from the deck during this procedure. The adjunct is adhered to the cartridge deck with an attachment material, which needs to be sticky or tacky enough to keep the adjunct adhered to the deck, but not so sticky that it is difficult to detach from the deck after the stapling procedure is completed. As such, the present retainer systems provide solutions that ensure the adjunct is properly adhered to the staple cartridge right before the staple cartridge is positioned at the treatment site. These systems provide such solutions by incorporating retainers and retainer systems that enable a temporary compressive force to be applied to implantable adjuncts on staple cartridges before they are used in surgery.

The invention is not necessarily limited to the examples described, which can be varied in construction and detail. The terms "distal" and "proximal" are used throughout this description and are meant to refer to positions and directions relative to the handle of surgical instrument 200. As such, "distal" or distally" refer to a position distant to or a direction away from the handle of surgical instrument 200 (i.e., a direction toward a patient). Similarly, "proximal" or "proximally" refer to a position near or a direction towards the handle of surgical instrument 200 (i.e., toward an operator of the handle). Furthermore, the singular forms "a," "an," and "the" include plural referents unless the context clearly dictates otherwise. Furthermore, the use of "couple", "coupled", or similar phrases should not be construed as being limited to a certain number of components or a particular order of components unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 71% to 109%.

As used herein, the term "cam" can refer to any surface designed to cause movement of another component when the cam is moved. For example, "cam" can be used to refer to an eccentric edge, a ramp, a protrusion, a secondary retainer, a sleeve, etc. that is configured to cause a cartridge or a retainer to compress an adjunct against a cartridge.

The components described herein can be formed from biocompatible materials using manufacturing methods known to those of skill in the art. For example, and not limitation, the components described herein can be molded from a thermoplastic.

FIG. 1 provides background on how the presently described retainer systems improve upon prior designs because the presently-disclosed systems take into account an adjunct being positioned on the staple cartridge. Referring now to the figure, FIG. 1 shows an exploded view of a prior staple cartridge 100 that does not include an implantable adjunct on deck 108 thereof. In these prior examples, retainer 50 can be attached to staple cartridge 100 from proximal end 102 to distal end 104 to ensure that staples within various staple pockets 110 do not fall out of openings 112 within deck 108. Retainer 50, therefore, is merely a static device with a function of preventing staples from falling out before staple cartridge 100 is positioned within channel 206 of first jaw frame 204 of end effector 202. Retainer 50 is simply removed when staple cartridge 100 is inserted between channel rails 208 of channel 206.

Figure 2A:
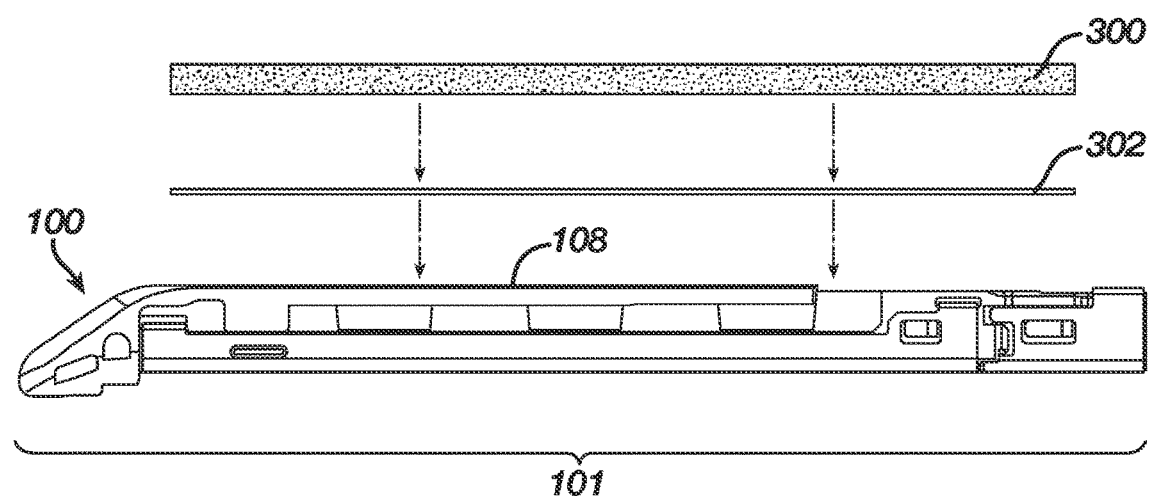
FIG. 2A is a schematic view showing a replaceable staple cartridge, an attachment material, and an implantable adjunct, according to aspects of the present disclosure.
Figure 2B:
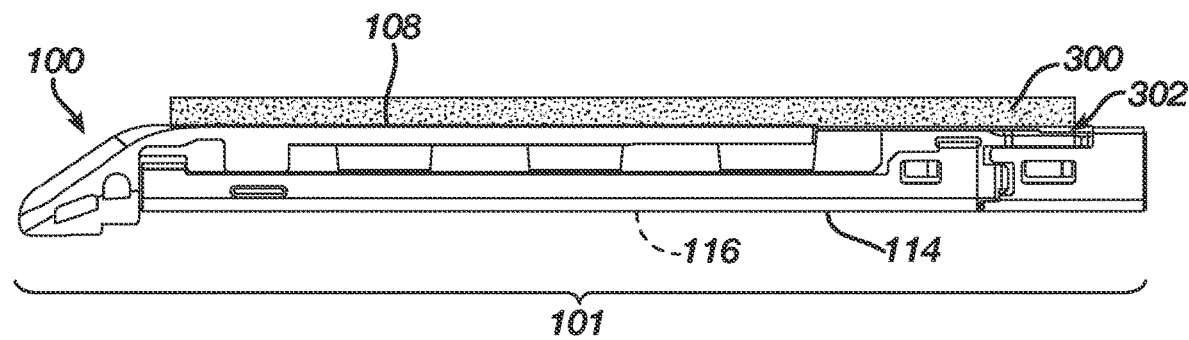
FIG. 2B is a schematic view showing the replaceable staple cartridge, attachment material, and implantable adjunct of FIG. 2A assembled, according to aspects of the present disclosure.
Figure 2C:
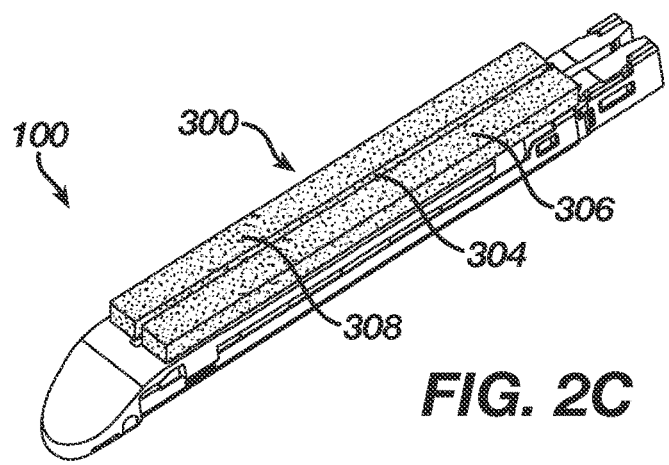
FIG. 2C is a perspective view of the assembled staple cartridge, attachment material, and implantable adjunct shown in FIG. 2B, according to aspects of the present disclosure.

FIGS. 2A-2C illustrate staple cartridges that include an implantable adjunct. As seen in the exploded view of FIG. 2A, the system includes staple cartridge 100 (which is substantially similar to the staple cartridge shown in FIG. 1) and implantable adjunct 300 which is adhered to deck 108 that is positioned along elongate body 101 of staple cartridge 100. Adjunct 300 can be adhered to staple cartridge 100 with attachment material 302. As described above, attachment material 302 can provide sufficient adhesion for adjunct 300 to remain adhered to deck 108 when being positioned at the treatment site, but the adhesion does not impair the ability of adjunct 300 from being detached from deck 108 when being implanted. In some instances, attachment material can be an adhesive, adhesive strip, double-sided tape, and the like. The attachment material 302 can be or include a pressure sensitive adhesive such that applying pressure to the adjunct 300 causes the attachment material 302 to be compressed and increases the adhesion of the attachment material 302 to the cartridge 100 and the adjunct 300. In other words, compression of the adjunct 300 against the cartridge 100 (several different methods are disclosed throughout this disclosure) increases the adhesion of the adjunct 300 to the cartridge 100 via the attachment material 302. The compression of the attachment material 302 can be less than a second and greatly increases the adhesion of the adjunct 300 to the cartridge.

FIG. 2B shows adjunct 300 adhered to deck 108 via attachment material 302. FIG. 2C is a perspective view of adjunct 300 adhered to deck 108. For background, the staples of the systems described herein are fired through adjunct 300 during the stapling procedure. In some instances, adjunct 300 can include sled groove 304 within length 350 of the adjunct. Sled groove 304 provides a path for a knife (not shown in figures) to traverse such that the knife does not need to cut through adjunct 300, thereby preserving the edge on the knife. When adjunct 300 includes sled groove 304, adjunct 300 can be considered to be separated into adjunct first side 306 and adjunct second side 308. In some examples, adjunct 300 can include laminated layers, such as a foam and/or porous material laminated with a mesh material, wherein the sled groove 304 is disposed in the foam and/or porous material but the mesh material remains intact. In other examples, adjunct 300 can include a film layer and/or a mesh layer. The film layer can comprise material commonly used with absorbable monofilament sutures and can be heat processed with a mesh layer to act as a bonding agent to hold the mesh and foam of the adjunct 300 together.

FIG. 3A is a side-view schematic of staple cartridge 100 being loaded into a surgical instrument, i.e., surgical instrument 200. Staple cartridge 100 is loaded into end effector 202 before being positioned at the treatment site. As described above, staple cartridge 100 is inserted into first jaw frame 204. Anvil 210 clamps down toward staple cartridge 100 during the stapling procedure. Once the tissue is stapled, anvil 210 opens to leave the staples and adjunct attached to the tissue. Staple cartridge 100 remains in first jaw frame 204 as surgical instrument 200 is removed from the treatment site. Although FIG. 3A shows staple cartridge 100 without a retainer attached thereto, the example retainers (i.e., retainer 400) described herein can be inserted into first jaw frame 204 while attached to the staple cartridge 100.

As stated above, implantable adjunct 300 can account for this differing tissue thickness by providing support for the thinner sections of tissue. Where the tissue is thick, implantable adjunct 300 can be compressed all the way down since no additional thickness is needed to account for the staple length. Where the tissue is thin, the implantable adjunct 300 is not as compressed, meaning the adjunct provides the additional thickness needed to account for the staple length, thereby providing proper compression in that section of the tissue. FIG. 3B is a schematic showing the implantable adjunct 300 stapled to tissue (T) having different thickness. The individual staples 120a,b,c,d have the same height (H), so the implantable adjunct 300 fills in the space for thinner sections of tissue (i.e., the tissue (T) shown at staples 120b and 120d). For thicker sections of tissue (i.e., the tissue (T) shown at staples 120a and 120c), the implantable adjunct 300 is more compressed as the staples do not need the additional space (i.e., height) filled in by the implantable adjunct 300.

Referring now to FIGS. 4A, 4B, 4C, and 4D, the example implementation shows a staple cartridge and retainer system that can protect an adjunct during shipment of the staple cartridge and also provide a compressive force to the adjunct. Retainer 400 includes first retainer tab 406 and second retainer tab 408 disposed between proximal end 402 and distal end 404 of retainer 400. Retainer 400 provides protection of adjunct 300, which is disposed along deck 108 of staple cartridge 100 (see FIGS. 2A-2C for views of staple cartridge 100). First retainer tab 406 and second retainer tab 408 are connected to retainer 400 and each define a lumen extending therethrough (i.e., first retainer tab lumen 407 and second retainer tab lumen 409). A retainer cam actuator 410 is configured to extend through the first retainer tab lumen 407 and second retainer tab lumen 409 and be positioned beneath the cartridge 100. In this way, the retainer 400 can be secured around the cartridge 100 to protect the adjunct 300.

Figure 4A:
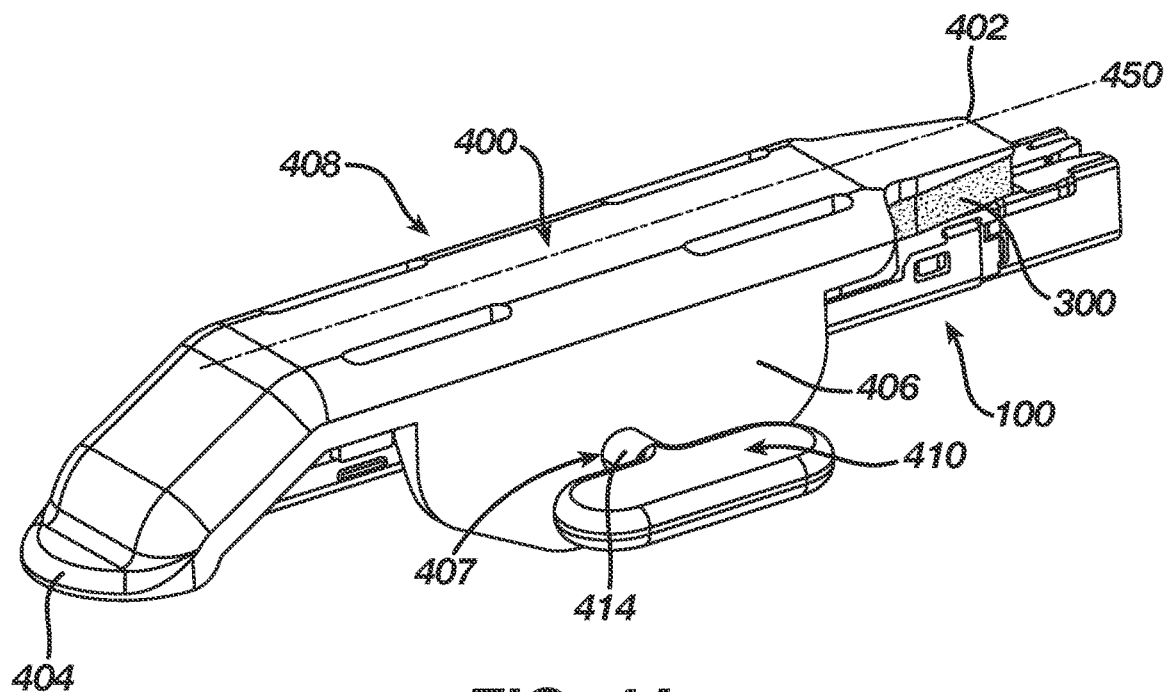
FIG. 4A is a perspective view of an example staple cartridge retainer with a cam, according to aspects of the present disclosure.
Figure 4B:
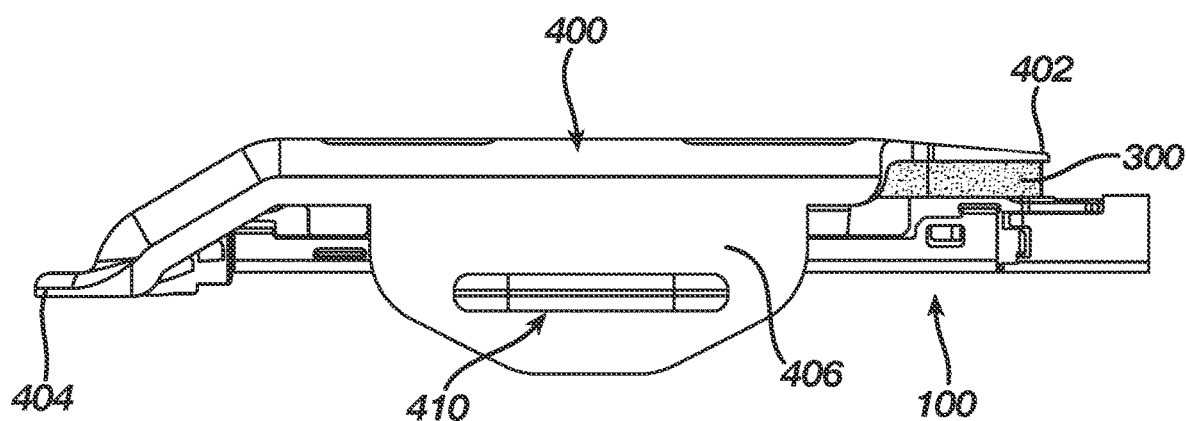
FIG. 4B is a side view of the example staple cartridge retainer shown in FIG. 4A, according to aspects of the present disclosure.
Figure 4C:
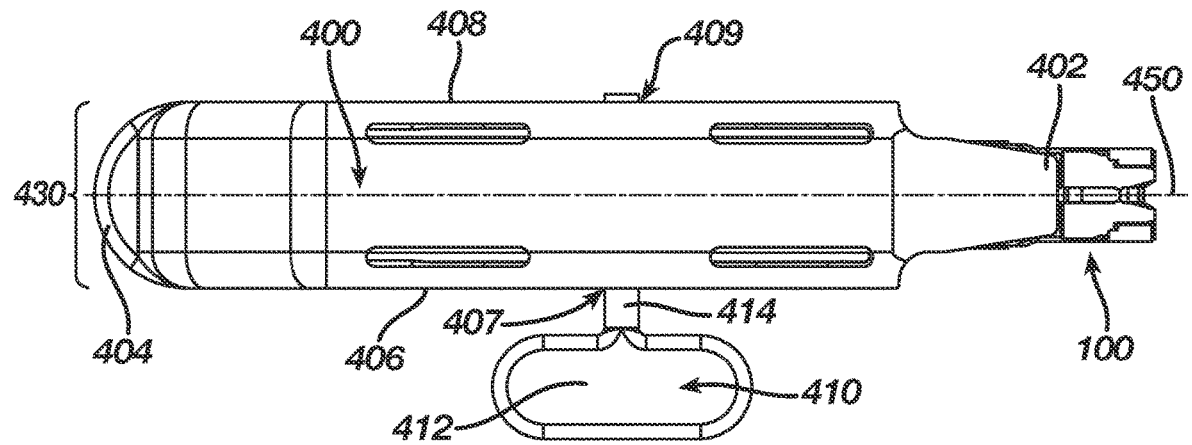
FIG. 4C is a top view of the example staple cartridge retainer shown in FIG. 4A, according to aspects of the present disclosure.

To provide the beneficial compressive force to adjunct 300, the retainer cam actuator 410 can be configured to be rotated and cause the cartridge 100 to be moved toward the retainer 400 to cause the retainer 400 to press the adjunct 300 against the deck 108 of the cartridge 100. The retainer cam actuator 410 comprises a retainer cam actuator handle 412 that is configured to be gripped and twisted by a user. The retainer cam actuator handle 412 is attached to a shaft 414 comprising a shaft proximal end 416 and a shaft distal end 418 (as shown in FIG. 4E). The shaft 414 includes an eccentric edge 420 that acts as a cam surface to cause the compressive force to adjunct 300. The shaft 414 comprises a generally circular profile while the eccentric edge 420 comprises a generally elliptical profile (as shown in FIG. 4F). In this way, as the retainer cam actuator 410 is rotated about a cam longitudinal axis 460, the eccentric edge 420 will push upward on the cartridge 100 to cause a compressor force to be applied to the adjunct 300. The retainer cam actuator 410 is aligned approximately in the middle of the cartridge 100 such that the retainer cam actuator 410 causes the entire cartridge 100 to move toward the retainer 400, rather than just one end of the cartridge 100.

The retainer cam actuator 410 can be configured such that the retainer cam actuator 410 is locked to the retainer 400 in a first position and removable from the retainer 400 in a second position. For example, the retainer cam actuator 410 can be configured such that a user must twist the retainer cam actuator handle 412 before the cartridge 100 can be removed from the retainer 400. For example, the retainer cam actuator 410 can include a threaded end such that the retainer cam actuator 410 cannot be slid along the cam longitudinal axis 460 and removed from the first retainer tab lumen 407 and the second retainer tab lumen 409 until the retainer cam actuator 410 has been sufficiently rotated to disengage from the threaded end. As another example, the retainer cam actuator 410 can include channels or other shapes formed into at least a portion of the shaft 414 that align with at least one of the first retainer tab 406 and second retainer tab 408 and configured such that the retainer cam actuator 410 must be rotated before the retainer 400 can be removed from the cartridge 100.

Although the retainer cam actuator 410 is shown as having a retainer cam actuator handle 412 much like a key, it will be appreciated that a lever, wheel, or other similar component can be used in place of the retainer cam actuator handle 412 to actuate the retainer cam actuator 410. Furthermore, as shown in FIG. 4C the retainer 400 and the elongate body 101 of the cartridge 100 can together form an envelope 430 and the retainer cam actuator 410 can extend beyond the outer edges of the envelope 430. In this way, a user is able to grip and rotate the retainer cam actuator 410.

Figure 4D:
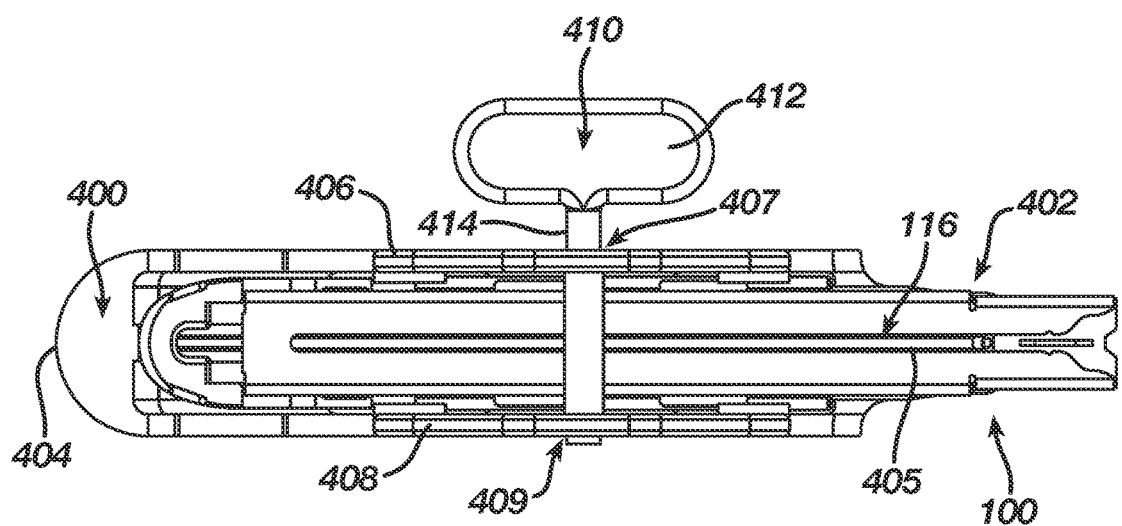
FIG. 4D is a bottom view of the example staple cartridge retainer shown in FIG. 4A, according to aspects of the present disclosure.
Figure 4E:
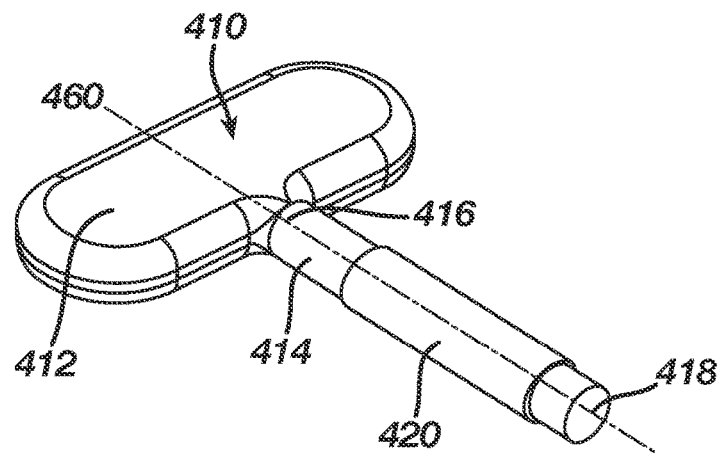
FIG. 4E is a perspective view of the cam shown in FIGS. 4A-4D, according to aspects of the present disclosure.
Figure 4F:
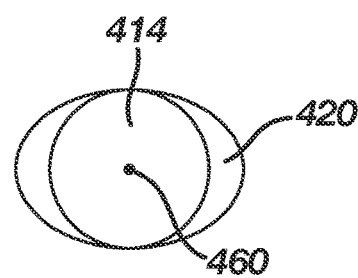
FIG. 4F is an end view of the cam shown in FIGS. 4A-4E, according to aspects of the present disclosure.
Figure 4G:
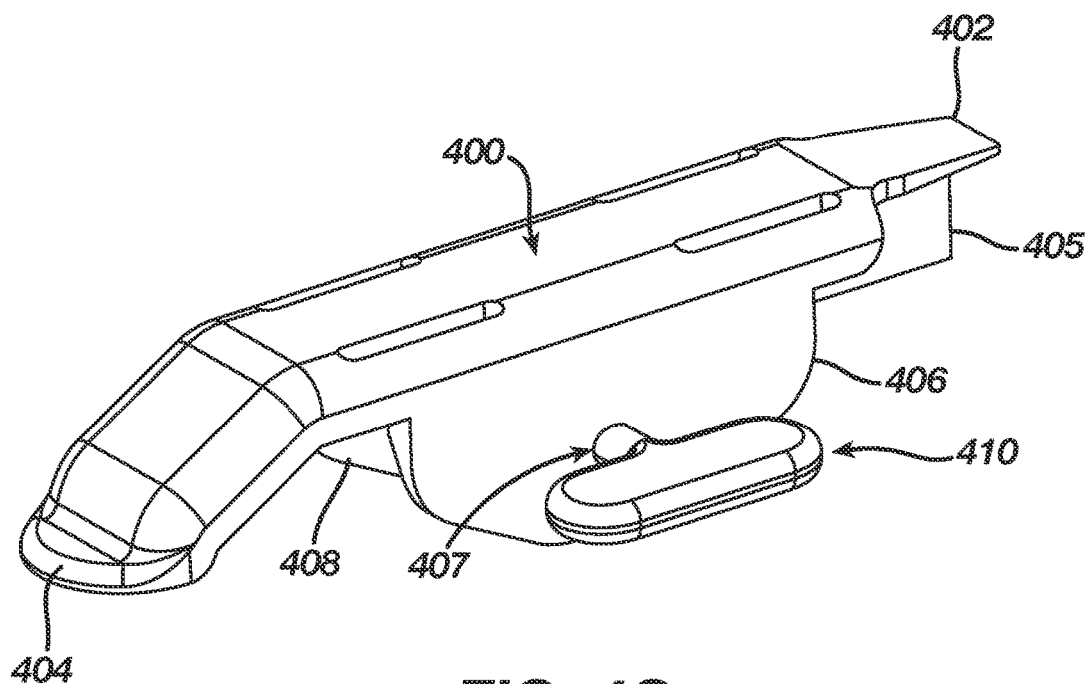
FIG. 4G is a perspective view of the retainer and cam shown in FIGS. 4A-4D with a staple cartridge removed, according to aspects of the present disclosure.

The retainer 400 includes a retainer rib 405 (as shown in FIGS. 4D and 4G) that extends downwardly from approximately a center line of the retainer 400. The retainer rib 405 can be configured to extend into the sled groove 304 of the adjunct 300 and into sled channel 116 (as shown in FIG. 4D) through which the sled 118 can slide. As will be appreciated, the sled 118 can be configured to slide along the cartridge 100 and cause one or more staples 120 to extend through the stable pocket openings 112.

The retainer cam actuator 410 can be assembled with the retainer 400 at the factory and shipped to the end user with the retainer cam actuator 410 such that the user must actuate the retainer cam actuator 410 prior to removal of the retainer 400 from the cartridge 100. In other examples, it will be appreciated, that the retainer cam actuator 410 can be separate from the retainer 400 and inserted into the first retainer tab lumen 407 and the second retainer tab lumen 409 for actuation of the eccentric edge 420 to compress the adjunct 300 against the cartridge 100.

Figure 5:
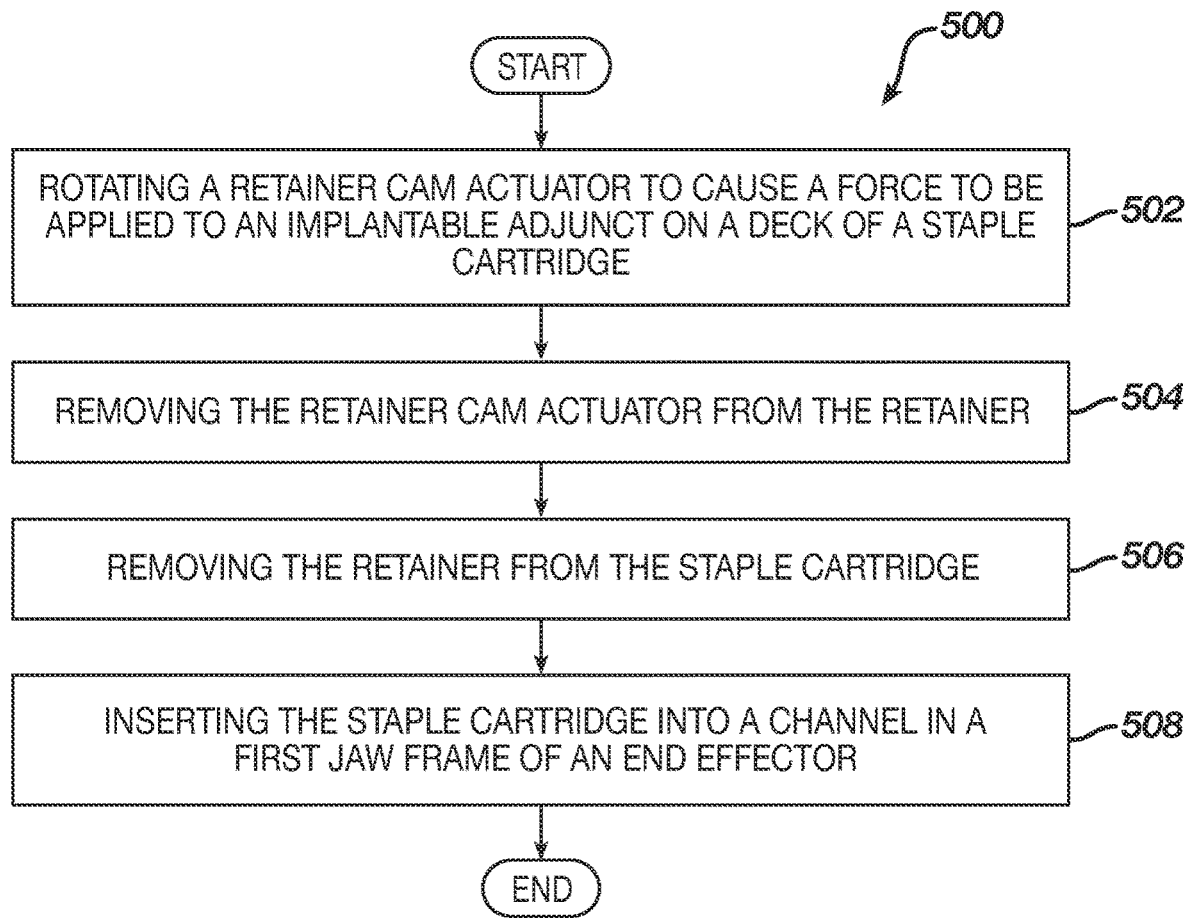
FIG. 5 is a flow chart illustrating a method of causing a retainer to compress an implantable adjunct against a deck of a staple cartridge, according to aspects of the present disclosure.

FIG. 5 is a flowchart for an example method 500 of loading a staple cartridge 100 onto an end effector 202, according to aspects of the present disclosure. Method 500 can be performed to remove the retainer 400 shown in FIGS. 4A-4G from the cartridge 100 and load the cartridge 100 into an end effector 202 (see FIG. 3 for end effector 202). Method 500 includes rotating 502 a retainer cam actuator (e.g., retainer cam actuator 410) to cause a force to be applied to an implantable adjunct on a deck of a staple cartridge. The method 500 includes removing 504 the retainer cam actuator from the retainer, removing 506 the retainer from the staple cartridge, and inserting 508 the staple cartridge into a channel in a first jaw frame of an end effector. Although the example 500 is described as having the retainer removed from the cartridge prior to insertion of the cartridge into the channel of the first jaw frame of the end effector, it will be appreciated that the retainer can alternatively be removed after insertion of the cartridge into the channel.

Figure 6A:
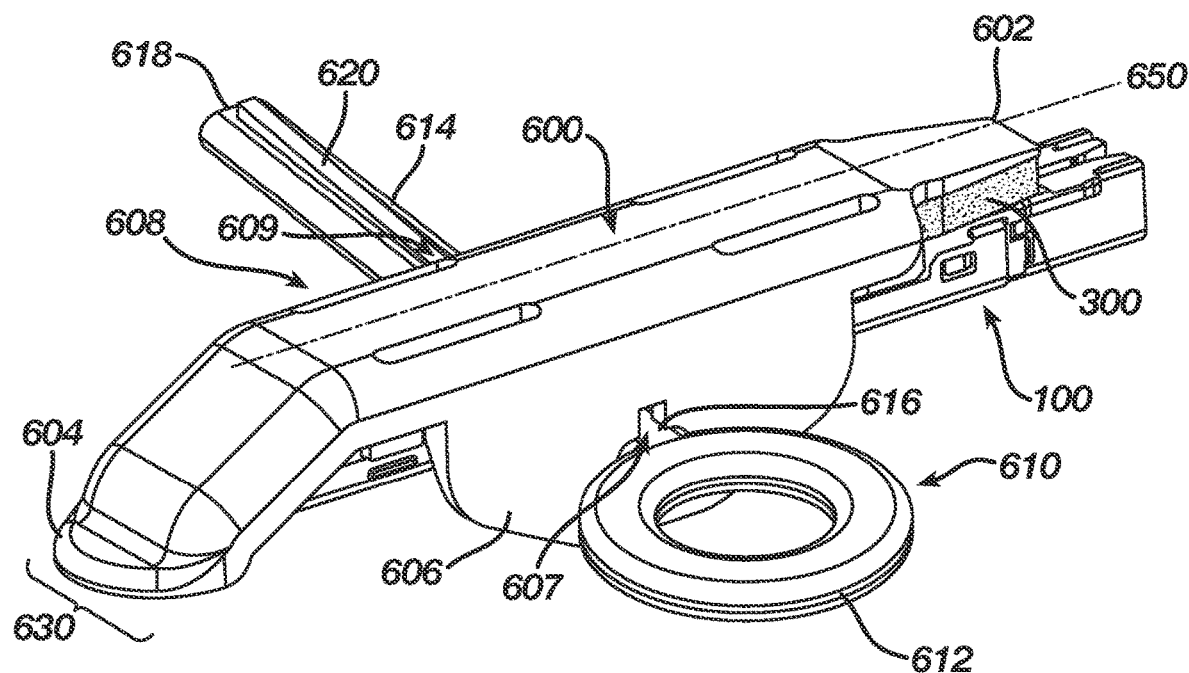
FIG. 6A is a perspective view of another example staple cartridge retainer with a cam, according to aspects of the present disclosure.
Figure 6B:
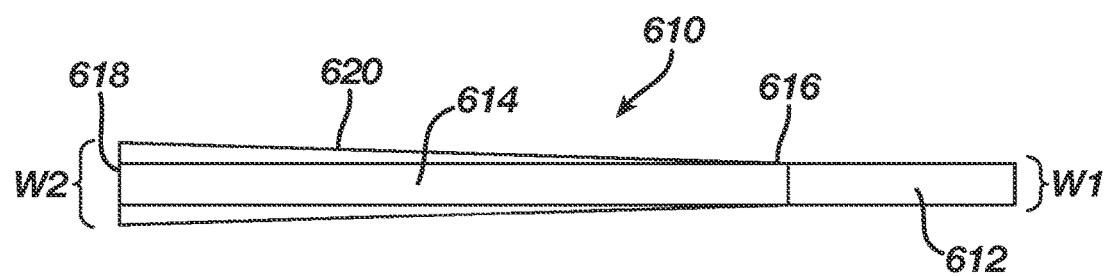
FIG. 6B is a side view of the cam shown in FIG. 6A, according to aspects of the present disclosure.

Turning now to FIGS. 6A and 6B, the example implementation shows a staple cartridge and retainer system, similar to the example shown in FIGS. 4A-4G, that can protect an adjunct during shipment of the staple cartridge and also provide a compressive force to the adjunct. Retainer 600 similarly includes a first retainer tab 606 and second retainer tab 608 disposed between proximal end 602 and distal end 604 of retainer 600. Retainer 600 provides protection of adjunct 300, which is disposed along deck 108 of staple cartridge 100 (see FIGS. 2A-2C for views of staple cartridge 100). First retainer tab 606 and second retainer tab 608 are connected to retainer 600 and each define a lumen extending therethrough (i.e., first retainer tab lumen 607 and second retainer tab lumen 609). A ramp cam 610 is configured to extend through the first retainer tab lumen 607 and second retainer tab lumen 609 and be positioned beneath the cartridge 100. In this way, the retainer 600 can be secured around the cartridge 100 to protect the adjunct 300.

To provide the beneficial compressive force to adjunct 300, the ramp cam 610 can be configured to slide and cause the cartridge 100 to be moved toward the retainer 600 to cause the retainer 600 to press the adjunct 300 against the deck 108 of the cartridge 100. The ramp cam 610 comprises a ramp cam handle 612 that is configured to be gripped and pulled by a user. The ramp cam handle 612 is attached to a ramp shaft 614 comprising a shaft proximal end 616 and a shaft distal end 618 (as shown in FIG. 6B). The ramp shaft 614 includes a ramp 620 that has a first end nearer the proximal end 616 that has a height that is less than a second end of the ramp 620 that is nearer the distal end 618. In other words, the ramp cam 610 can have a first width W1 near the proximal end 616 and second width W2 near the distal end 618, the second width W2 can be greater than the first width W1. In this way, as a user pulls the ramp cam 610 from the retainer 600, the ramp 620 will push on the cartridge 100 and cause the cartridge 100 to push against the retainer 600 to cause a compressive force on the adjunct 300. In other words, the ramp cam 610 can be slidable between a first position in which the adjunct 300 is not compressed between the cartridge 100 and the retainer 600 and a second position in which the adjunct 300 is compressed between the cartridge 100 and the retainer 600.

Similar to the retainer cam actuator 410, although the ramp cam 610 is shown as having a ramp cam handle 612 much like a key, it will be appreciated that a lever, knob, or other similar component can be used in place of the ramp cam handle 612 to actuate the ramp cam 610. Furthermore, as shown in FIG. 6A the retainer 600 and the elongate body 101 of the cartridge 100 can together form an envelope 630 and the ramp cam 610 can extend beyond the outer edges of the envelope 630. In this way, a user is able to grip and pull the ramp cam 610.

Figure 7:
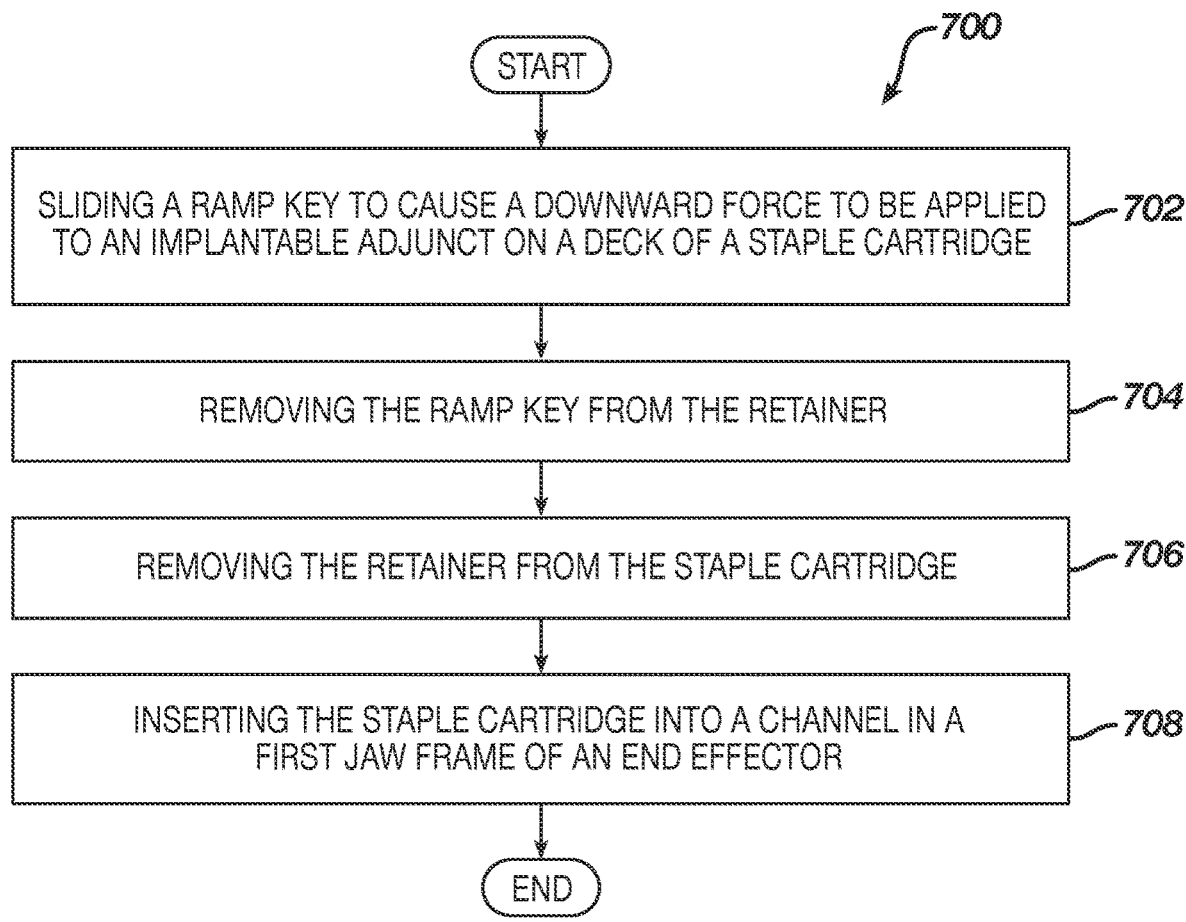
FIG. 7 is another flow chart illustrating a method of causing a retainer to compress an implantable adjunct against a deck of a staple cartridge, according to aspects of the present disclosure.

FIG. 7 is a flowchart for an example method 700 of loading a staple cartridge 100 onto an end effector 202, according to aspects of the present disclosure. Method 700 can be performed to the remove the retainer 600 shown in FIGS. 6A and 6B from the cartridge 100 and load the cartridge 100 into an end effector 202 (see FIG. 3 for end effector 202). Method 700 includes sliding 702 a ramp cam (e.g., ramp cam 610) to cause a force to be applied to an implantable adjunct on a deck of a staple cartridge. The method 700 includes removing 704 the ramp cam from the retainer, removing 706 the retainer from the staple cartridge, and inserting 708 the staple cartridge into a channel in a first jaw frame of an end effector. Although the example 500 is described as having the retainer removed from the cartridge prior to insertion of the cartridge into the channel of the first jaw frame of the end effector, it will be appreciated that the retainer can alternatively be removed after insertion of the cartridge into the channel.

Figure 8A:
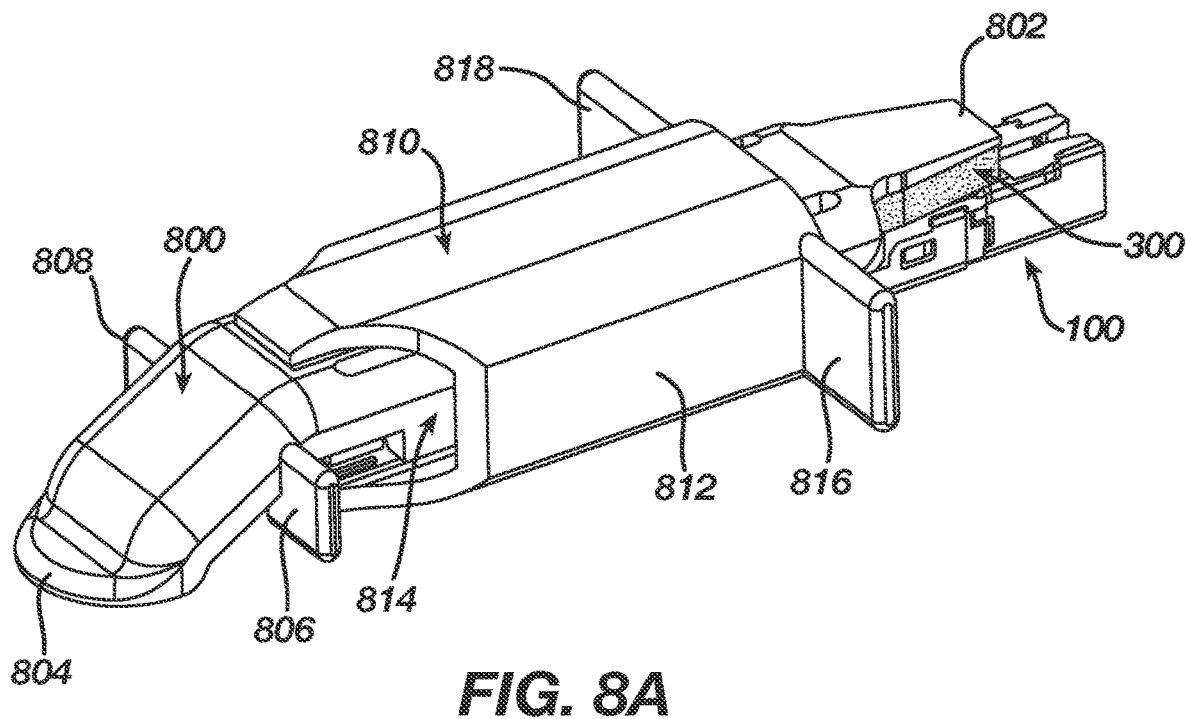
FIG. 8A is a perspective view of another example staple cartridge retainer with a cam, according to aspects of the present disclosure.
Figure 8B:
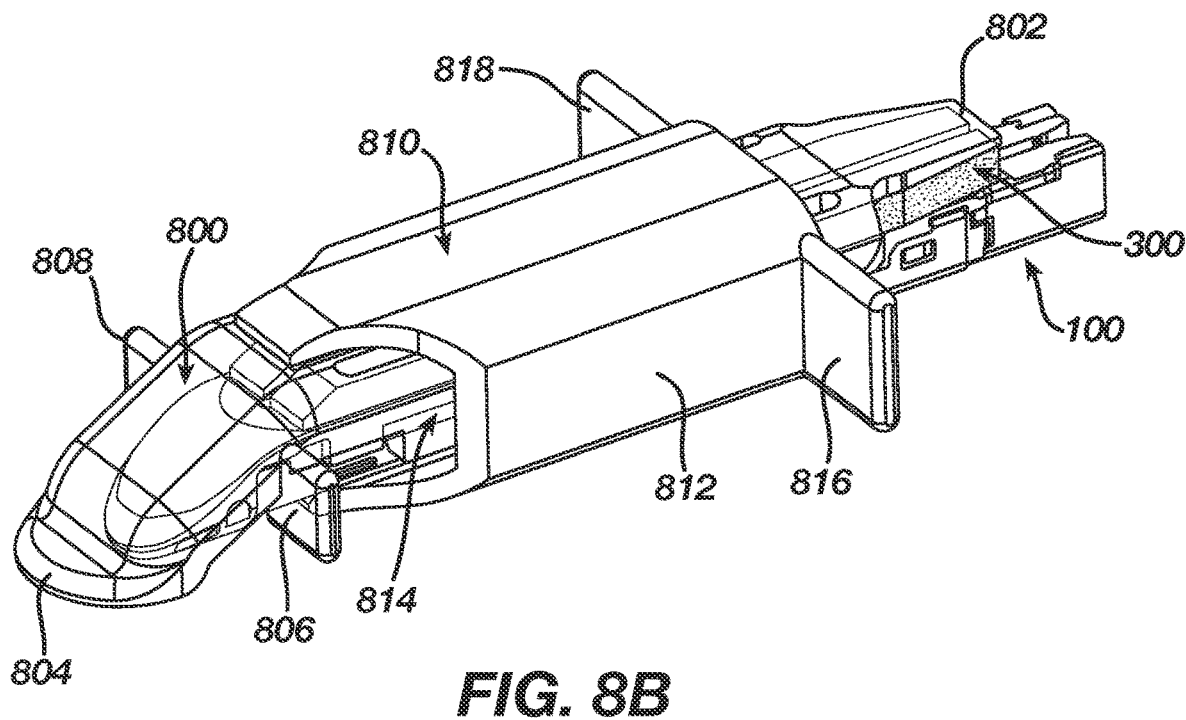
FIG. 8B is another perspective view of the example staple cartridge retainer with a cam shown in FIG. 8A with the retainer being shown as semi-transparent, according to aspects of the present disclosure.

FIGS. 8A and 8B illustrate another example of a retainer 800 and a cam 810 configured to cause a compressive force on an adjunct 300 against a cartridge 100. FIG. 8B shows the retainer 800 as semi-transparent to show the adjunct 300 disposed between the retainer 800 and the cartridge 100. In this example, the retainer 800 comprises a retainer proximal end 802, a retainer distal end 804, a retainer first tab 806, and a retainer second tab 808. The cam 810 includes a cam body 812 that defines a cam lumen 814 extending therethrough. The cam 810 can similarly include a cam first tab 816 and a cam second tab 818. In this example, the cam lumen 814 can be sized such that the retainer 800 and the cartridge 100 can fit within the cam lumen 814 and the retainer 800 and cartridge 100 can be pushed against each other to compress the adjunct 300 while disposed in the cam lumen 814. The retainer 800, cam 810, and cartridge 100 can be assembled together at a factory prior to shipment to the end user such that the cam 810 causes the retainer 800 and cartridge 100 to be pressed toward each other to compress the adjunct 300 against the cartridge 100 until the cam 810 and retainer 800 are removed just prior to use of the cartridge 100.

To remove the cam 810 and retainer 800 from the cartridge 100, a user grips the retainer first tab 806, retainer second tab 808, cam first tab 816, and cam second tab 818 and pulls the cam 810 toward the proximal end 802 of the retainer 800 until the cam 810 slides off of the retainer 800. Alternatively, the cam 810 and retainer 800 can be configured such that the cam 810 is slid toward the distal end 804 for removal of the cam 810. Once the cam 810 is removed from the retainer 800, the retainer 800 can be removed from the cartridge 100. The adjunct 300 will have been sufficiently pressed against the deck 108 of the cartridge 100 due to having been compressed between the retainer 800 and the cartridge 100 in the cam lumen 814.

Figure 9:
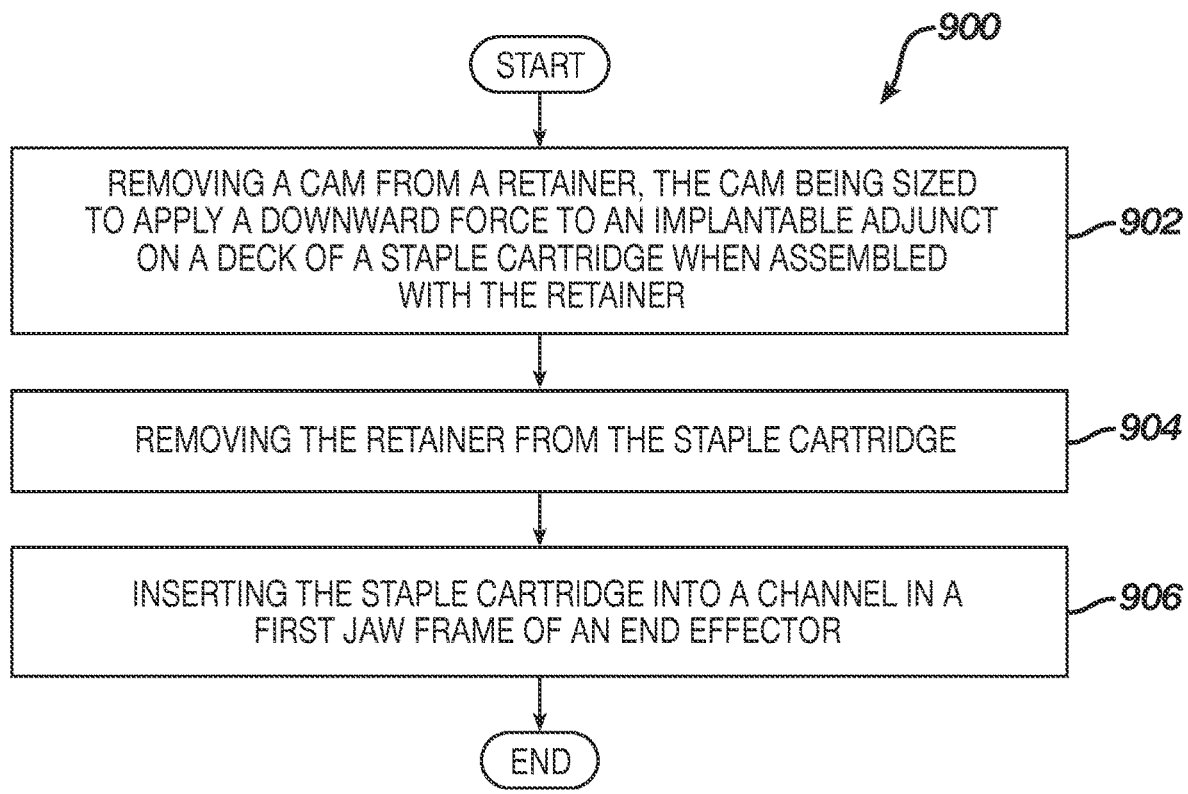
FIG. 9 is yet another flow chart illustrating a method of causing a retainer to compress an implantable adjunct against a deck of a staple cartridge, according to aspects of the present disclosure.

FIG. 9 is a flowchart for an example method 900 of loading a staple cartridge 100 onto an end effector 202, according to aspects of the present disclosure. Method 900 can be performed to remove the retainer 800 shown in FIGS. 8A and 8B from a cartridge 100 and load the cartridge 100 into an end effector 202 (see FIG. 3 for end effector 202). Method 900 includes removing 902 a cam (e.g., cam 810) from a retainer (e.g., retainer 800), the cam being sized to apply a force to an implantable adjunct on a deck of a staple cartridge when assembled with the retainer. The method 900 includes removing 904 the retainer from the staple cartridge, and inserting 906 the staple cartridge into a channel in a first jaw frame of an end effector. Although the example 500 is described as having the retainer removed from the cartridge prior to insertion of the cartridge into the channel of the first jaw frame of the end effector, it will be appreciated that the retainer can alternatively be removed after insertion of the cartridge into the channel.

Figure 10A:
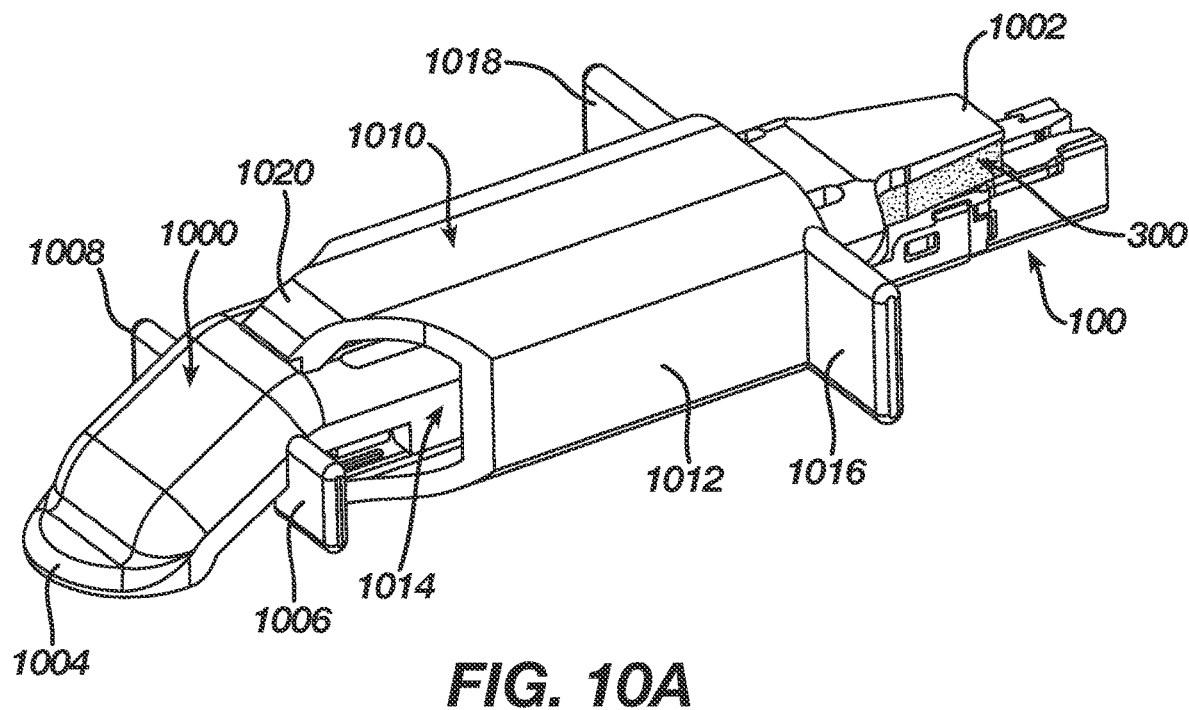
FIG. 10A is a perspective view of another example staple cartridge retainer with a cam, according to aspects of the present disclosure.
Figure 10B:
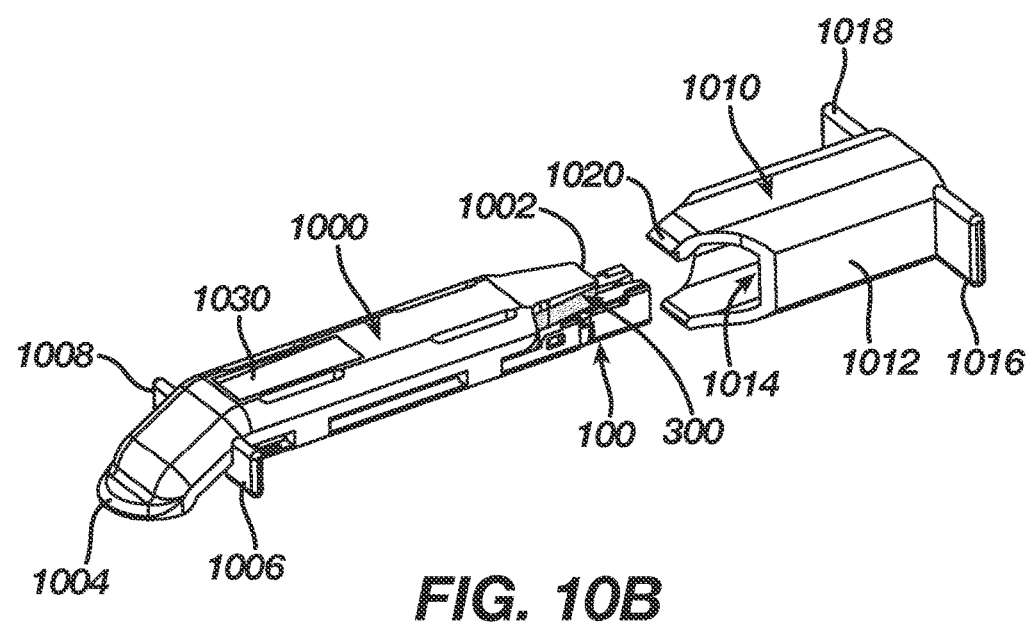
FIG. 10B is a partially exploded view of the staple cartridge retainer and cam shown in FIG. 10A, according to aspects of the present disclosure.

Turning now to FIGS. 10A and 10B, the disclosed technology can include a retainer 1000 similar to the retainer 800 and a cam 1010 similar to the cam 810. The retainer 1000 can similarly include a retainer proximal end 1002, a retainer distal end 1004, a retainer first tab 1006, and a retainer second tab 1008. Similarly, the cam 1010 can include a cam body 1012 defining a cam lumen 1014 extending therethrough as well as a cam first tab 1016 and a cam second tab 1018. The cam 1010 however, can differ from the cam 810 by the cam lumen 1014 being sized such that the retainer 1000, cartridge 100, and adjunct 300 can be placed therein without the adjunct 300 being compressed. In other words, the cam lumen 1014 is not sized to cause compression of the adjunct 300 while the retainer 1000, cartridge 100, and adjunct 300 are disposed therein.

The cam 1010 further includes a cam lip 1020 that extends inwardly toward the cam lumen 1014 as shown in FIGS. 10A and 10B. The retainer 1000 differs from the retainer 800 by including a retainer ramp 1030 that is configured to align with the cam lip 1020. The cam lip 1020 is configured to extend inwardly and engage with the retainer ramp 1030 such that the cam lip 1020 pushes the retainer 1000 toward the cartridge 100 to compress the adjunct 300 when the cam 1010 is removed from the retainer 1000.

The retainer ramp 1030 is configured to form a ramped surface that extends upwardly in the direction in which the cam 1010 will be removed from the retainer 1000. In the example, shown in FIGS. 10A and 10B, the retainer ramp 1030 extends upwardly from the distal end 1004 toward the proximal end 1002 although it will be appreciated that the cam 1010 can be configured to be removed from the retainer 1000 in a direction from the proximal end 1002 toward the distal end 1004 and the retainer ramp 1030 can be configured to extend upwardly from the proximal end 1002 toward the distal end 1004. The retainer ramp 1030 can have a low end that is at a depth in the retainer 1000 such that the cam lip 1020 extends into the retainer ramp 1030 but does not push the retainer 1000 to move toward the cartridge 100 and cause compression of the adjunct 300. Thus, the cam 1010 and retainer 1000 can be configured to protect the cartridge 100 and adjunct 300 while assembled but not necessarily cause the adjunct 300 to be compressed until the cam 1010 is removed from the retainer 1000. When the cam 1010 is removed from the retainer 1000, the cam lip 1020 will slide along the retainer ramp 1030. Because the retainer ramp 1030 slopes upwardly in the direction in which the cam 1010 is removed from the retainer 1000, the cam lip 1020 will engage with the retainer ramp 1030 as it slides along the retainer ramp 1030 and thereby cause the retainer 1000 to move toward the cartridge 100 to compress the adjunct 300 against the cartridge.

Figure 11:
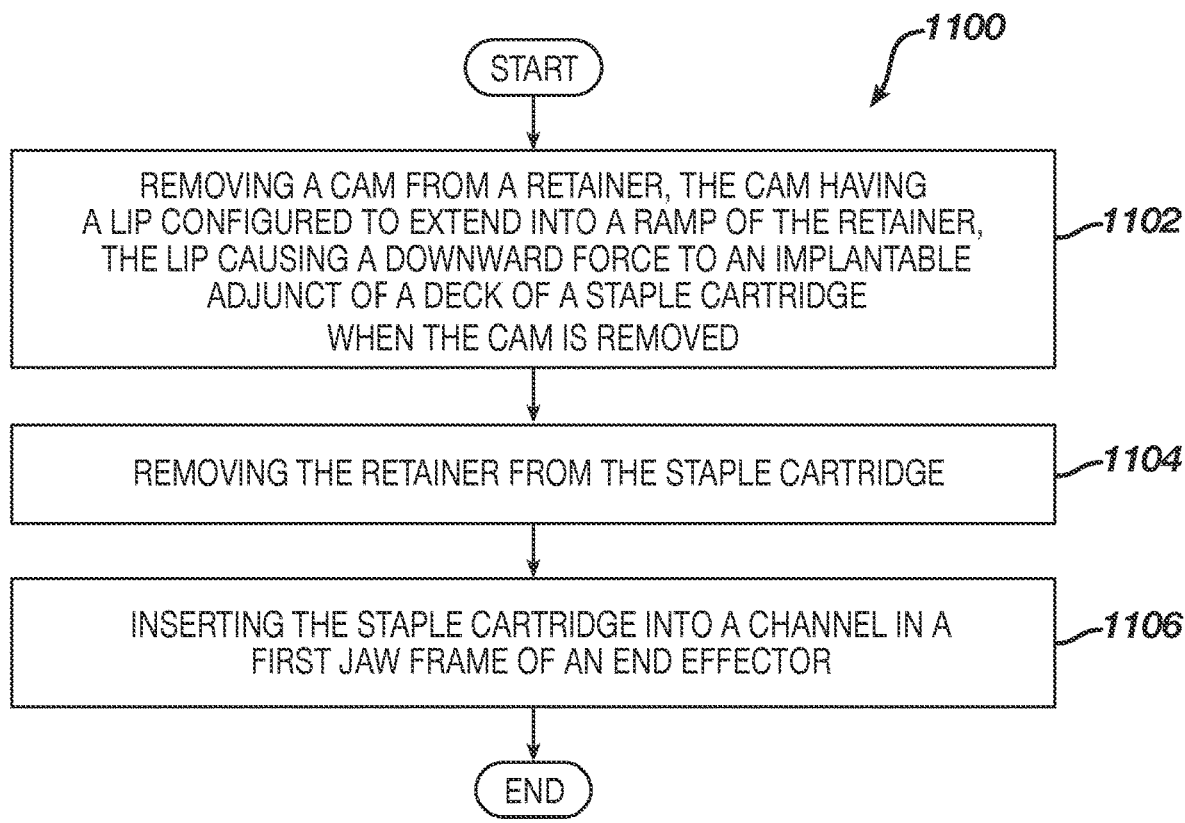
FIG. 11 is another flow chart illustrating a method of causing a retainer to compress an implantable adjunct against a deck of a staple cartridge, according to aspects of the present disclosure.

FIG. 11 is a flowchart for an example method 1100 of loading a staple cartridge 100 onto an end effector 202, according to aspects of the present disclosure. Method 1100 can be performed to remove the retainer 1000 shown in FIGS. 10A and 10B from a cartridge 100 and load the cartridge 100 into an end effector 202 (see FIG. 3 for end effector 202). Method 1100 includes removing 1102 a cam (e.g., cam 1010) from a retainer (e.g., retainer 1000), the cam comprising a lip configured to extend into a ramp of the retainer to apply a force to an implantable adjunct on a deck of a staple cartridge when assembled with the retainer. The method 1100 includes removing 904 the retainer from the staple cartridge and inserting 1106 the staple cartridge into a channel in a first jaw frame of an end effector. Although the example 500 is described as having the retainer removed from the cartridge prior to insertion of the cartridge into the channel of the first jaw frame of the end effector, it will be appreciated that the retainer can alternatively be removed after insertion of the cartridge into the channel.

Examples of the present disclosure can be implemented by any of the following numbered clauses:

Clause 1: A staple cartridge (100), comprising: an elongate body (101), the elongate body (101) comprising a deck (108), the elongate body (101) defining a plurality of staple pockets (110), each of the staple pockets (110) accessible via an opening (112) defined by the deck (108); an implantable adjunct (300) removably secured to the deck (108); and a retainer (400, 600, 800, 1000) removably securable to the elongate body (101), the retainer (400, 600, 800, 1000) moveable through a range of motion relative to the elongate body (101) while the retainer (400, 600, 800, 1000) is secured to the elongate body (101), with the retainer (400, 600, 800, 1000) secured to the elongate body (101), the implantable adjunct (300) positioned intermediate the retainer (400, 600, 800, 1000) and the elongate body (101), a movement of the retainer (400, 600, 800, 1000) through at least a portion of the range of motion compressing the implantable adjunct (300) against the deck (108) of the elongate body (101); and a cam (410, 610, 810, 1010) movably connected to the elongate body (101) when the retainer (400, 600, 800, 1000) is secured to the elongate body (101), the cam (410, 610, 810, 1010) positioned and arranged to selectively actuate the retainer (400, 600, 800, 1000) along the range of motion, with the retainer (400, 600, 800, 1000) secured to the elongate body (101) the cam (410, 610, 810, 1010) being actuatable from a first position to a second position to actuate the retainer (400, 600, 800, 1000) along the range of motion.

Clause 2: The staple cartridge of clause 1, wherein, with the retainer (400, 600) secured to the elongate body (101), the retainer (400, 600) and the elongate body (101) together define an envelope (430, 630), the cam (410) extending beyond the envelope (430, 630).

Clause 3: The staple cartridge of any one of the preceding clauses, wherein, with the cam (410, 610, 810, 1010) secured to the retainer (400, 600, 800, 1000), the implantable adjunct (300) and the elongate body (101) are positioned intermediate the retainer (400, 600, 800, 1000) and the cam (410, 610, 810, 1010).

Clause 4: The staple cartridge of any one of the preceding clauses, wherein the cam (410, 610, 810, 1010) is locked to the retainer (400, 600, 800, 1000) in the first position and removeable from the retainer (400, 600, 800, 1000) in the second position.

Clause 5: The staple cartridge of any one of the preceding clauses, wherein the cam (410) is rotatable with respect to the retainer (400) between the first position and the second position to contact a bottom surface of the elongate body (101) and compress an entire length of the implantable adjunct (300) against the deck (108) of the elongate body (101).

Clause 6: The staple cartridge of clause 5, wherein the cam (410) comprises an eccentric edge (420).

Clause 7: The staple cartridge of clause 5 or 6, wherein the cam (410) is slidable with respect to the retainer (400) to remove the cam (410) from the retainer (400).

Clause 8: The staple cartridge (100) of any one of clauses 5-7, the retainer (400, 600) further comprising: a first retainer tab (406) defining a first retainer tab lumen (407) extending therethrough; and a second retainer tab (408) defining a second retainer tab lumen (409) extending therethrough, the cam (410) configured to extend through the first retainer tab lumen (407) and the second retainer tab lumen (409).

Clause 9: The staple cartridge of any one of clauses 1-4, wherein the cam (610, 810, 1010) is slidable with respect to the retainer (600, 800, 1000) between the first position and the second position to compress an entire length of the implantable adjunct (300) against the deck (108) of the elongate body (101).

Clause 10: The staple cartridge (100) of clause 9, the retainer (600) further comprising: a first retainer tab (606) defining a first retainer tab lumen (607) extending therethrough; and a second retainer tab (608) defining a second retainer tab lumen (609) extending therethrough, the cam (610) configured to extend through the first retainer tab lumen (607) and the second retainer tab lumen (609).

Clause 11: The staple cartridge of clause 10, wherein the cam (610) comprises a ramp (620) including a first width (W1) at a proximal end (616) and a second width (W2) at a distal end (618), the second width (W2) being greater than the first width (W1).

Clause 12: The staple cartridge of clause 9, the retainer (1000) further comprising a ramp (1030) and the cam (1010) comprising a lip (1020), wherein, when the cam (1010) is slid along the retainer (1000), the lip (1020) is configured to slide along the ramp (1030) to cause the retainer (1000) to compress the implantable adjunct (300) against the deck (108) of the elongate body (101).

Clause 13: The staple cartridge of any one of clauses 1-4, the cam (810) comprising a lumen (814) extending therethrough, the lumen (814) being sized to at least partially receive the elongate body (101), the implantable adjunct (300), and the retainer (800) to cause the retainer (800) to compress the implantable adjunct (300) against the deck (108) of the elongate body (101).

Clause 14: The staple cartridge of any one of the preceding clauses in combination with an end effector (202), the end effector (202) comprising a channel (206), the staple cartridge seatable in the channel (206) with the cam (410, 610, 810, 1010) removed from the retainer (400, 600, 800, 1000).

Clause 15: The staple cartridge (100) of any one of the preceding clauses, the implantable adjunct (300) comprising a sled groove (304) separating the implantable adjunct (300) into a first side (306) and a second side (308), the retainer (400, 600, 800, 1000) further comprising a rib (405) configured to extend into the sled groove (304).

Clause 16: A method of causing a retainer (400, 600, 1000) to compress an implantable adjunct (300) against a deck (108) of an elongated body, the method comprising: actuating a cam (410, 610, 1010) between a first position and a second position to actuate a retainer (400, 600, 1000) of a staple cartridge along a range of motion relative to an elongate body (101) of the staple cartridge to cause the retainer (400, 600, 1000) to compress an implantable adjunct (300) against a deck (108) of the elongate body (101); removing the cam (410, 610, 1010) from the retainer (400, 600, 1000); removing the retainer (400, 600, 1000) from the elongate body (101); and inserting the elongate body (101) into a channel (206) of an end effector (202).

Clause 17: The method of clause 16, actuating the cam (410) comprises rotating the cam (410) between the first position and the second position.

Clause 18: The method of clause 16, actuating the cam (610, 1010) comprises sliding the cam (410) between the first position and the second position.

Clause 19: The method of clause 18, the cam (610) comprising a ramp (620) including a first width (W1) at a proximal end (616) and a second width (W2) at a distal end (618), the second width (W2) being greater than the first width (W1).

Clause 20: A staple cartridge (100), comprising: an elongate body (101), the elongate body (101) having a deck (108), the elongate body (101) defining a plurality of staple pockets (110), each of the staple pockets (110) accessible via an opening (112) defined by the deck (108); an implantable adjunct (300) removably secured to the deck (108); and a retainer (800) removably securable to the elongate body (101), the retainer (800) configured to compress the implantable adjunct (300) against the deck (108) of the elongate body (101); and a cam (810) comprising a lumen (814) extending therethrough, the lumen (814) configured to at least partially receive the elongate body (101), the implantable adjunct (300), and the first retainer (800) and to cause the first retainer (800) to compress the implantable adjunct (300) against the deck (108) of the elongate body (101).

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A staple cartridge, comprising:
   an elongate body, the elongate body comprising a deck, the elongate body defining a plurality of staple pockets, each of the staple pockets accessible via an opening defined by the deck;
   an implantable adjunct removably secured to the deck; and
   a retainer removably securable to the elongate body, the retainer moveable through a range of motion relative to the elongate body while the retainer is secured to the elongate body,
      with the retainer secured to the elongate body, the implantable adjunct positioned intermediate the retainer and the elongate body,
      a movement of the retainer through at least a portion of the range of motion compressing the implantable adjunct against the deck of the elongate body; and
   a cam movably connected to the elongate body when the retainer is secured to the elongate body, the cam positioned and arranged to selectively actuate the retainer along the range of motion, with the retainer secured to the elongate body the cam being actuatable from a first position to a second position to actuate the retainer along the range of motion.

2. The staple cartridge of claim 1, wherein, with the retainer secured to the elongate body, the retainer and the elongate body together define an envelope, the cam extending beyond the envelope.

3. The staple cartridge of claim 1, wherein, with the cam secured to the retainer, the implantable adjunct and the elongate body are positioned intermediate the retainer and the cam.

4. The staple cartridge of claim 1, wherein the cam is locked to the retainer in the first position and removeable from the retainer in the second position.

5. The staple cartridge of claim 1, wherein the cam is rotatable with respect to the retainer between the first position and the second position to contact a bottom surface of the elongate body and compress an entire length of the implantable adjunct against the deck of the elongate body.

6. The staple cartridge of claim 5, wherein the cam comprises an eccentric edge.

7. The staple cartridge of claim 5, wherein the cam is slidable with respect to the retainer to remove the cam from the retainer.

8. The staple cartridge of claim 5, the retainer further comprising:
   a first retainer tab defining a first retainer tab lumen extending therethrough; and
   a second retainer tab defining a second retainer tab lumen extending therethrough, the cam configured to extend through the first retainer tab lumen and the second retainer tab lumen.

9. The staple cartridge of claim 1, wherein the cam is slidable with respect to the retainer between the first position and the second position to compress an entire length of the implantable adjunct against the deck of the elongate body.

10. The staple cartridge of claim 9, the retainer further comprising:
    a first retainer tab defining a first retainer tab lumen extending therethrough; and
    a second retainer tab defining a second retainer tab lumen extending therethrough, the cam configured to extend through the first retainer tab lumen and the second retainer tab lumen.

11. The staple cartridge of claim 10, wherein the cam comprises a ramp including a first width at a proximal end and a second width at a distal end, the second width being greater than the first width.

12. The staple cartridge of claim 9, the retainer further comprising a ramp and the cam comprising a lip, wherein, when the cam is slid along the retainer, the lip is configured to slide along the ramp to cause the retainer to compress the implantable adjunct against the deck of the elongate body.

13. The staple cartridge of claim 1, the cam comprising a lumen extending therethrough, the lumen being sized to at least partially receive the elongate body, the implantable adjunct, and the retainer to cause the retainer to compress the implantable adjunct against the deck of the elongate body.

14. The staple cartridge of claim 1 in combination with an end effector, the end effector comprising a channel, the staple cartridge seatable in the channel with the cam removed from the retainer.

15. The staple cartridge of claim 1, the implantable adjunct comprising a sled groove separating the implantable adjunct into a first side and a second side, the retainer further comprising a rib configured to extend into the sled groove.

16. A method of causing a retainer to compress an implantable adjunct against a deck of an elongated body, the method comprising:
    actuating a cam between a first position and a second position to actuate a retainer of a staple cartridge along a range of motion relative to an elongate body of the staple cartridge to cause the retainer to compress an implantable adjunct against a deck of the elongate body;
    removing the cam from the retainer;
    removing the retainer from the elongate body; and
    inserting the elongate body into a channel of an end effector.

17. The method of claim 16, actuating the cam comprises rotating the cam between the first position and the second position.

18. The method of claim 16, actuating the cam comprises sliding the cam between the first position and the second position.

19. The method of claim 18, the cam comprising a ramp including a first width at a proximal end and a second width at a distal end, the second width being greater than the first width.

20. A staple cartridge, comprising:
- an elongate body, the elongate body having a deck, the elongate body defining a plurality of staple pockets, each of the staple pockets accessible via an opening defined by the deck;
- an implantable adjunct removably secured to the deck; and
- a retainer removably securable to the elongate body, the retainer configured to compress the implantable adjunct against the deck of the elongate body; and
- a cam comprising a lumen extending therethrough, the lumen configured to at least partially receive the elongate body, the implantable adjunct, and the retainer and to cause the retainer to compress the implantable adjunct against the deck of the elongate body.

* * * * *